United States Patent [19]

Malakhoff et al.

[11] Patent Number: 4,798,085
[45] Date of Patent: Jan. 17, 1989

[54] TEST RIG FOR EXAMINING SEAL FINGER WEAR

[75] Inventors: Alexander Malakhoff, Arlington, Va.; Sydney Davis, Silver Spring, Md.

[73] Assignee: The United States of America as represented by the Secretary of the Navy, Washington, D.C.

[21] Appl. No.: 403,263

[22] Filed: Jul. 29, 1982

[51] Int. Cl.⁴ .................. B63B 9/08; G01M 10/00
[52] U.S. Cl. ........................... 73/148; 73/865.6
[58] Field of Search .................. 73/148, 432 SD

[56] References Cited

U.S. PATENT DOCUMENTS

| | | | |
|---|---|---|---|
| 3,333,465 | 8/1967 | Goodman | 73/148 |
| 3,693,421 | 9/1972 | Karper et al. | 73/101 |
| 3,859,841 | 1/1975 | Evans et al. | 73/12 |
| 4,044,598 | 8/1977 | Stavovy et al. | 73/7 |

FOREIGN PATENT DOCUMENTS 55-71930  5/1980  Japan ..................... 73/148

Primary Examiner—William A. Cuchlinski, Jr.
Assistant Examiner—Thomas B. Will
Attorney, Agent, or Firm—L. A. Marsh; T. E. McDonnell

[57] ABSTRACT

A test rig for measuring wear on flexible membrane material used as seal fingers on air cushion vehicles includes a pump and nozzle for producing a shallow, high speed water flow and hydraulic actuators for moving the seal fingers into the flow. The fingers are moved into and out of the flow to simulate the effect of the ship crossing waves at high speed. A fan and air plenum inflate the seal fingers in a manner similar to normal operation.

1 Claim, 2 Drawing Sheets

TEST RIG FOR EXAMINING SEAL FINGER WEAR

BACKGROUND OF THE INVENTION

1. Field of the Invention

This invention relates generally to a testing apparatus and method and more specifically to an apparatus and method for testing flexible membrane material used as seal fingers on air cushion vehicles.

2. Description of the Prior Art

Ships which travel across water supported by a bubble of air, such as air cushion vehicles (hovercraft) and surface effect ships, generally have a flexible structure for containing the air bubble on which it rides. One conventional arrangement utilizes an inflated bag which receives the air from the lift fan and seal fingers which descend from the bag and are in contact with the water. The seal fingers are made from flexible membrane material which flexes in reaction to waves on the water surface. This flexing eventually causes the failure of the material and the seal fingers must periodically be replaced.

The complex motions which these fingers undergo and the relation between failure and the various parameters of this motion are of great interest to designers of such ships. Unfortunately, there has been no testing apparatus capable of realistically reproducing the flexural motion of the seal finger so that parameters may be measured under laboratory conditions. This lack of information has hindered the development of better designs of seal fingers and development of operational standards for ships to avoid damage.

One previous attempt to test the material included horizontally attaching one end of a strip of material to a solid base with air blowing underneath the strip. The air causes the strip to flap in a manner similar to a flag, causing a flexing of the material. A second similar test uses a strip mounted in a similar fashion but with the second end bent and fastened to a weight. Air and water flowing along the inside bend of the strip causes a flexing and vibrating motion of the strip.

Other attempts at testing include shooting jets of water either continuously or in pulses at pieces of material. In one version the material is placed over a frame to achieve the same shape as in a ship and with air filling the finger from behind. All of these test procedures measure the endurance of the material due to a particular type of bending. Unfortunately, the forces involved and the type of bending performed bear no resemblance to the forces and bending encountered in actual performance. The shape of the finger itself, the drag forces encountered as the finger touches the water and the force and frequency of waves are not considered or tested at all in these procedures.

SUMMARY OF THE INVENTION

Accordingly, one object of the invention is to provide a new and improved apparatus and method for testing seal fingers for air-cushion vehicles.

Another object of this invention is to provide realistic forces and movements on seal fingers during testing.

A further object of the invention is to make accurate and realistic measurement of parameters which affect the life of seal fingers.

Another object of the invention is to provide movement of a seal finger in a stream of water to simulate the action of waves and the movement of the ship.

Briefly, these and other objects of the invention are achieved by providing a shallow, high speed water flow channel into which a test seal finger may be placed. An even flow is provided by a pump and diffuser system. The test seal may be moved into and out of the flow to simulate actual running conditions. A fan and plenum assembly keeps the finger inflated.

BRIEF DESCRIPTION OF THE DRAWINGS

A more complete appreciation of the invention and many of the attendant features thereof will be readily appreciated as the same becomes better understood by reference to the following detailed description when considered in connection with the accompanying drawings wherein.

DETAILED DESCRIPTION OF THE DRAWINGS

Figure 1:
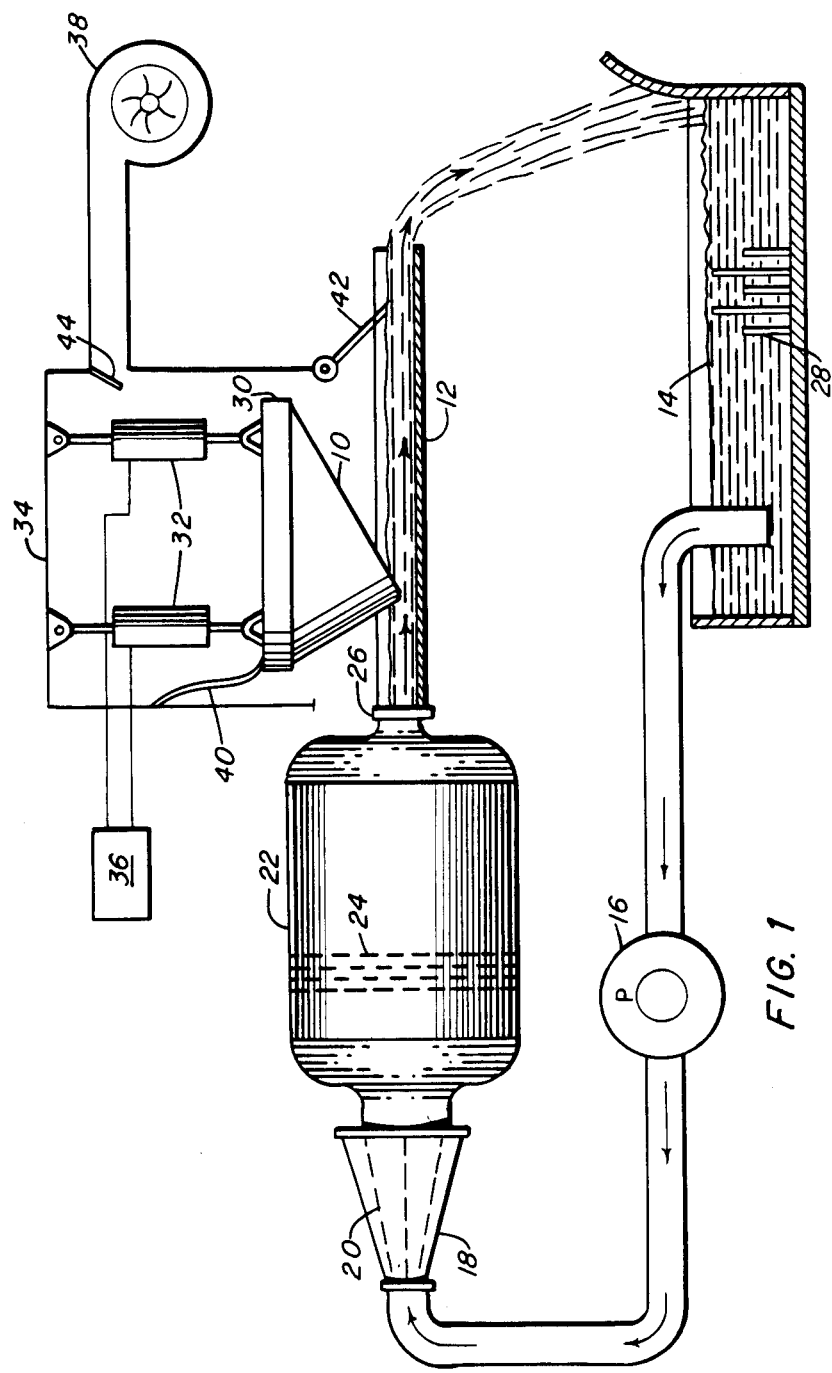
FIG. 1 is a schematic diagram of the invention.

Referring now to the drawings wherein like references characters designate identical or corresponding parts throughout the several views and more particularly to FIG. 1 wherein the overall arrangement of the various functional elements of the instant invention is shown as including an inflatable seal finger 10 to be tested in a water channel 12. Water (or other fluid) is drawn from a reservoir 14 by pump 16 and fed as an input to diffuser 18. The diffuser includes guide vanes 20 for directing the flow of water within the diffuser. The water proceeds from the diffuser 18 to the nozzle chamber 22, which contains baffles 24 to reduce flow turbulence. The output of the nozzle chamber is formed into a nozzle having an opening with the horizontal dimension being much larger than the vertical dimension. The water leaving the nozzle creates a shallow high speed flow in channel 12. Spent water flows back into the reservoir for recycling. Baffles 28 are present in the reservoir to reduce turbulence.

The seal finger 10 is held at the top by a rigid frame 30 to support the seal finger in its normal working position. The frame 30 may be moved up and down by means of actuators 32, whose upper ends are fixed to a rigid structure 34. The actuators move according to instructions received from controller 36. The controller may be instructed to produce any up and down motion desired by the tester.

Rigid structure 34 encloses the actuator mechanism 32 and the seal finger 10. Fan 38 pressurizes the inside of the structure so as to inflate the seal finger. Flexible partition 40 connects the front wall of the rigid structure 34 to the top of the frame 30 to prevent leakage of air around the front of the fingers. The other walls may have similar partitions or the frame may hold a sliding seal in contact with the walls. A gate 42 at the rear of the rigid structure allows water to escape through the channel but retains most of the pressurized air. Valve 44 allows air to be blown into the structure but prevents back flow when the fan is off.

Figure 2:
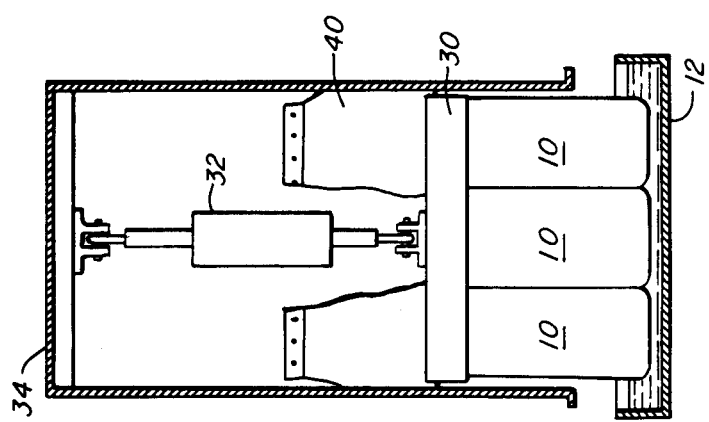
FIG. 2 is a cross sectional view of part of the invention shown in FIG. 1.

FIG. 2 shows a cross section of the rigid structure 34 and the apparatus contained therein. Three seal fingers are carried by the frame 30 with the center finger being the test specimen. The outer fingers are present to make the test environment similar to seal fingers in actual use on a ship where a series of fingers are arranged side by side.

Figure 3:
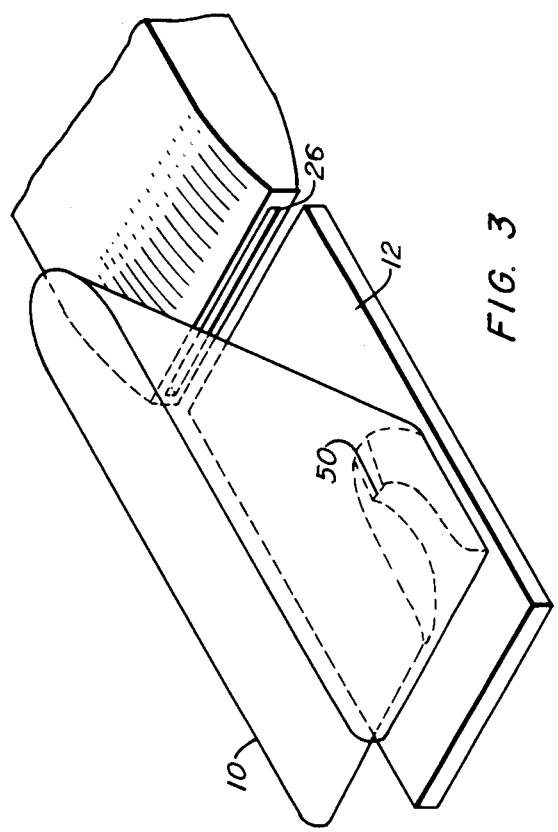
FIG. 3 is a diagram showing the deflection of the seal finger.

The seal finger under test undergoes a deformation when placed in the flow of water as shown in FIG. 3. Water flowing out of nozzle 26 forms a high speed shallow stream flowing along channel 12. The bottom part of seal finger 10 is in contact with the water flow which causes the bottom of the finger to buckle upwardly forming bump 50.

The testing may be operated in a manner to highly simulate the action of the sea on the seal fingers of an air cushion vehicle. The controller 36 may be programmed or manually operated to make the movements of the seal finger realistic. In particular, it is possible to record the actual movements of such a vessel as it moves through the sea and use the recording as a model for operating the controller. The seal finger may be moved into and out of contact with the water at the same frequency as a real vessel to obtain realistic flexing patterns during the test.

The speed of the water in the channel may be varied to simulate travel at various speeds. The speed may be controlled by changing the speed of the pump or by a valving arrangement (not shown). By varying the speed of the water and the operation of the controller 36, studies may be conducted to determine what speed and motions are most detrimental to the seal fingers. Accordingly, better fingers may then be designed and existing vessels may be operated in a manner to give longer life to the seal fingers.

It is not necessary for the water in the channel to be more than a few inches deep. The speed of the water causes the bottom of the seal finger to bend up before hitting the bottom of the channel. The action of the water and the properties of the flexible material cause the formation of a buckled shape 50 in the bent portion of the seal finger. This bending closely simulates the shape of the seal finger in normal operation. In addition, it has been found that this buckled section vibrates at a high frequency causing the greatest amount of wear on the seal finger. This motion is apparently the main cause of failure in operational seal fingers and the reproduction of this effect in a test rig is vital to accurate results in wear measurements. It should now become clear why earlier attempts at testing have not been entirely successful. Mere bending of the material or squirting the material with a jet of water does not produce realistic bending motions of the material such as buckled area 50 and particularly like the high frequency vibrations of this area. Such motions are only reproduced when the finger is placed in a high speed stream of water as in the present invention. As a result, the failure rates observed and measured using the present invention compare favorably with actual failure rates of seal fingers in use on ships. This means that the experimenter may conduct controlled tests measuring wear as a function of various parameters such as the speed of the water and the vertical movement of the finger, thus providing valuable information for improved designs and better operation of the ships.

The diffuser 18 and nozzle chamber 22 provide a steady non-turbulent flow of water with no bubbles to the nozzle 26. The guide vanes 20 and baffles 24 are included to help achieve this kind of flow. The fan 38 is controlled to produce a pressure inside the seal fingers equal to that on a ship. The flexible partition 40 or other sealing devices prevent the pressurized air from escaping from the upper part of structure 34 without passing through the seal fingers. Actuators 32 have been shown as hydraulic devices, but may be any form of motive system such as pneumatic or electric actuating devices. The actuators may be moved together to produce a straight up and down motion or separately to produce a rolling and/or pitching motion corresponding to the real motions of a ship.

While the invention has been shown as being mounted on land, it is possible to mount the entire apparatus on a barge. This would remove the need for a fixed reservoir with baffles 28. It is only necessary to place the inlet pipe to pump 16 into the lake or sea where the barge floats and to return the water after being expelled from the channel 12.

The device under test may also be turned sideways so that the flow of water in the channel is directed against the side of the finger rather than the front. This simulates the action of a finger on a side of the air cushion vehicle. The actuators and seals may also be turned if desired.

Obviously many modifications and variations of this invention are possible in light of the above teachings. It is therefore to be understood that within the scope of the appended claims the invention may be practiced otherwise than as specifically described.

What is claimed is:

1. An apparatus for testing a seal finger for an air cushion vehicle comprising:
    a reservoir of water;
    a pump for pumping water from said reservoir;
    a diffuser connected to the output of said pump to prevent turbulence in the flow of water from said pump;
    a nozzle connected to said diffuser having a narrow opening for producing a high speed flow of water;
    a shallow channel for receiving said high speed flow of a water from said nozzle, said channel returning the water to said reservoir;
    means for holding said seal finger;
    means for moving said means for holding so that said seal finger moves into and out of contact with said flow of water;
    means for controlling said means for moving so as to simulate the motion of a ship moving through waves whereby the forces encountered by said seal finger in contact with said water flow simulate the forces encountered in actual use;
    an enclosure for covering said means for holding, said means for moving and said seal finger;
    a fan for forcing air into said enclosure so as to pressurize the interior of said enclosure;
    flexible means for connecting the walls of the enclosure with said means for holding so as to prevent pressurized air from escaping the enclosure except through the seal finger which is thereby inflated;
    whereby the seal finger is caused to wear in a manner similar to actual use so that accurate testing of the material is accomplished.

* * * * *